(12) United States Patent
Chen (10) Patent No.: US 8,329,757 B2
(45) Date of Patent: Dec. 11, 2012

(54) CURCUMIN ANALOG COMPOSITIONS AND RELATED METHODS

(75) Inventor: Danyang Chen, Oklahoma City, OK (US)

(73) Assignee: Charlesson, LLC, Oklahoma City, OK (US)

( * ) Notice: Subject to any disclaimer, the term of this patent is extended or adjusted under 35 U.S.C. 154(b) by 271 days.

(21) Appl. No.: 12/579,361

(22) Filed: Oct. 14, 2009

(65) Prior Publication Data

US 2010/0216859 A1 Aug. 26, 2010

Related U.S. Application Data

(60) Provisional application No. 61/105,284, filed on Oct. 14, 2008.

(51) Int. Cl.
- *A01N 35/00* (2006.01)
- *A61K 31/12* (2006.01)
- *C07C 303/00* (2006.01)
- *C07C 307/00* (2006.01)
- *C07C 309/00* (2006.01)
- *C07C 311/00* (2006.01)

(52) U.S. Cl. ............................. 514/679; 514/678; 558/47
(58) Field of Classification Search .................. None
See application file for complete search history.

(56) References Cited

U.S. PATENT DOCUMENTS

| | | | |
|---|---|---|---|
| 5,208,251 A | 5/1993 | Belliotti et al. | |
| 5,266,344 A | 11/1993 | Mimura et al. | |
| 6,900,356 B2 | 5/2005 | Gokaraju et al. | |
| 7,279,501 B2 | 10/2007 | Kim | |
| 7,282,523 B2 | 10/2007 | Kim | |
| 7,355,081 B2 | 4/2008 | Lee et al. | |
| 7,371,766 B2 | 5/2008 | Snyder et al. | |
| 2004/0037902 A1 | 2/2004 | Pandol et al. | |
| 2005/0209205 A1 | 9/2005 | Shih et al. | |
| 2006/0020027 A1 | 1/2006 | Balasubramanyam et al. | |
| 2006/0148905 A1 | 7/2006 | Kim | |
| 2007/0003641 A1 | 1/2007 | Kim | |
| 2007/0293507 A1 | 12/2007 | Baik et al. | |
| 2008/0033055 A1 | 2/2008 | Miller et al. | |
| 2008/0070974 A1 | 3/2008 | Reddy et al. | |
| 2008/0146660 A1 | 6/2008 | Lee et al. | |
| 2008/0161391 A1 | 7/2008 | Lee et al. | |
| 2008/0200478 A1 | 8/2008 | Robinson | |
| 2010/0048901 A1 | 2/2010 | Takahashi et al. | |
| 2010/0152493 A1* | 6/2010 | Shibata et al. | 568/325 |

FOREIGN PATENT DOCUMENTS

WO 2008-066151 A1 6/2008

OTHER PUBLICATIONS

Kim et al. (2010) The effect of Curcumin on Corneal Neovasculization in Rabbit Eyes. Current Eye Research, 35(4): 274-280.*
Watanabe D et al. (2005) Erythropoietin as a retinal angiogenic factor in proliferative diabetic retinopathy. N. Engl J Med. 353(8):. 782-792.*
Maines LW et al. (2006) Pharmacologic manipulation of sphingosine kinase in retinal endothelial cells: implications for angiogenic ocular diseases. Invest Ophthalmol Vis Sci 47: 5022-5031.*
Economopoulou M et al. (2005) Inhibition of pathologic retinal neovascularization by alpha-defensins. Blood 106: 3831-3838.*
Longeras R et al. (2012) A PEDF-derived peptide inhibits retinal neovascularization and blocks mobilization of bone marrow-derived endothelial progenitor cells. Exp Diabetes Res. 2012: Article ID 518426.*
Lee et al. (1998) Ocular Neovasculization: An Epidemiologic Review. 43(3):245-268.*
James R. Fuchs et al, Structure-activity Relationship Studies of Curcumin Analogues, 19 Bioorganic & Medicinal Chemistry Letters 2065-69 (2009).
Aggarwal, et al., "Curcumin (Diferuloylmethane) Down-Regulates Espression of Cell Proliferation and Antia poptotic and Metastatic Gene Products through Suppression of IkBa Kinase and Akt Activation," Mol Pharmacol,69:195:-206, 2006.
Fuchs, et.al., "Structure-activity relationship studies of curcumin analogues," Bioorganic & Medicinal Chemistry Letters, Feb. 2009, vol. 19,pp. 2065-2069.
Lui, et al., "Inhibition of Thioredoxin Reductase by Curcumin Analogs," Biosci. Biotechnol. Biochem., 72(8), 2214-2218, 2008.
International Search Report and Written Opinion for PCT/US2009/060726, dated May 7, 2010.

* cited by examiner

*Primary Examiner* — Bong-Sook Baek
(74) *Attorney, Agent, or Firm* — Scott E. Kamholz; Foley Hoag LLP (57) ABSTRACT

Novel curcumin-analog compounds are disclosed that are antioxidants useful in inhibition of pro-inflammation, angiogenic, and vascular permeability factors and elimination of reactive oxygen species. The curcumin compounds specifically inhibit VEGF and are useful in treating various diseases that are mediated through the oxidative stress pathway, including those that are characterized by inflammation, angiogenesis, or vascular leakage.

5 Claims, 3 Drawing Sheets

Fig. 1 wherein R₁ and R₂ are independently selected from the following table and may occupy one or more of the 2, 3, 5, or 6 positions on each respective aryl ring:

| $R_1$ | $R_2$ |
|---|---|
| H, lower alkyl, OH, OR$_4$, OAc | H, lower alkyl, OH, OR$_4$, OAc | wherein R3 is one of:

wherein $R_4$ is H or a lower alkyl; and wherein $R_5$ is H or a lower alkyl.

CURCUMIN ANALOG COMPOSITIONS AND RELATED METHODS

RELATED APPLICATIONS

This application incorporates by references and claims the priority of U.S. Provisional Application Ser. No. 61/105,284, filed on Oct. 14, 2008.

BACKGROUND

This application relates to novel curcumin-analogs having improved anti-inflammation, anti-angiogenic, anti-vascular permeability, and anti-cancer effects and inhibitory effects on reactive oxygen species.

SUMMARY

Novel curcumin-analog compounds are disclosed that are antioxidants useful in inhibition of pro-inflammation, angiogenic, vascular permeability factors and cancer and elimination of reactive oxygen species. CLT010 compounds specifically inhibit VEGF and are useful in treating various diseases that are mediated through the oxidative stress pathway.

According to a feature of the present disclosure, a composition is disclosed comprising an agent comprising at least one of the following:

and a pharmaceutically acceptable carrier.

According to a feature of the present disclosure, a method is disclosed comprising, providing an effective amount of an agent having the formula:

to an animal having need a disease.

According to a feature of the present disclosure, a method is disclosed comprising using at least one of the compounds having the formula:

for the manufacture of a medicament for therapeutic application to a patient having a disease.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, mechanical, biological, electrical, functional, and other changes may be made without departing from the scope of the present disclosure. The following detailed description is, therefore, not to be taken in a limiting sense, and the scope of the present disclosure is defined only by the appended claims. As used in the present disclosure, the term "or" shall be understood to be defined as a logical disjunction and shall not indicate an exclusive disjunction unless expressly indicated as such or notated as "xor."

As used herein, the term "eye-related disease" shall mean opthalmological diseases, including those characterized by at least one of inflammation, angiogenesis, neovascularization, or vascular leakage, or those diseases that are caused or worsened by oxidative stress.

As used herein, the term "effective amount" shall mean an amount of agent administered that effects a beneficial result in treating a disease in an animal.

As used herein, the term "compound" is intended to refer to a chemical entity, whether in the solid, liquid, or gaseous phase, and whether in a crude mixture or purified and isolated. The terms "alkyl," "alkene," and "alkoxy" include straight chain and branched alkyl, alkene, and alkoxy, respectively. The term "lower alkyl" refers to $C_1$-$C_4$ alkyl. The term "alkoxy" refers to oxygen substituted alkyl, for example, of the formulas —OR or —ROR$_1$, wherein R and R$_1$ are each independently selected alkyl. The terms "substituted alkyl" and "substituted alkene" refer to alkyl and alkene, respectively, substituted with one or more non-interfering substituents, such as but not limited to, $C_3$-$C_6$ cycloalkyl, e.g., cyclopropyl, cyclobutyl, and the like; acetylene; cyano; alkoxy, e.g., methoxy, ethoxy, and the like; lower alkanoyloxy, e.g., acetoxy; hydroxy; carboxyl; amino; lower alkylamino, e.g., methylamino; ketone; halo, e.g. chloro or bromo; phenyl; substituted phenyl, and the like. The term "halogen" includes fluorine, chlorine, iodine and bromine.

"Aryl" means one or more aromatic rings, each of 5 or 6 carbon atoms. Multiple aryl rings may be fused, as in naphthyl or unfused, as in biphenyl. Aryl rings may also be fused or unfused with one or more cyclic hydrocarbon, heteroaryl, or heterocyclic rings.

"Substituted aryl" is aryl having one or more non-interfering groups as substituents.

"Heteroaryl" is an aryl group containing from one to four N, O, S atoms(s), or a combination thereof, which heteroaryl group is optionally substituted at carbon or nitrogen atom(s) with $C_1$-$C_6$ alkyl, —CF$_3$, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, five-membered heteroaryls having one hetero atom (e.g., thiophenes, pyrroles, furans); five-membered heteroaryls having two heteroatoms in 1,2 or 1,3 positions (e.g., oxazoles, pyrazoles, imidazoles, thiazoles, purines); five-membered heteroaryls having three heteroatoms (e.g., triazoles, thiadiazoles); five-membered heteroaryls having three heteroatom; six-membered heteroaryls with one heteroatom (e.g., pyridine, quinoline, isoquinoline, phenanthrine, 5,6-cycloheptenopyridine); six-membered heteroaryls with two heteroatoms (e.g., pyridazines, cinnolines, phthalazines, pyrazines, pyrimidines, quinazolines); six-membered heteroaryls with three heteroatoms (e.g., 1,3,5-triazine); and six-membered heteroaryls with four heteroatoms.

"Substituted heteroaryl" is heteroaryl having one or more non-interfering groups as substituents.

"Heterocycle" or "heterocyclic" means one or more rings of five, six, or seven atoms with or without unsaturation or aromatic character and at least one ring atom which is not carbon. Preferred heteroatoms include sulfur, oxygen, and nitrogen. Multiple rings may be fused, as in quinoline or benzofuran.

"Substituted heterocycle" is heterocycle having one or more side chains formed from non-interfering substituents.

"Non-interfering substituents" are those groups that yield stable compounds. Suitable non-interfering substituents or radicals include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_7$-$C_{12}$ aralkyl, $C_7$-$C_{12}$ alkaryl, $C_3$-$C_{10}$ cycloalkyl, $C_3$-$C_{10}$ cycloalkenyl, phenyl, substituted phenyl, toluoyl, xylenyl, biphenyl, $C_2$-$C_{12}$ alkoxyalkyl, $C_7$-$C_{12}$ alkoxyaryl, $C_7$-$C_{12}$ aryloxyalkyl, $C_6$-$C_{12}$ oxyaryl, $C_1$-$C_6$ alkylsulfinyl, $C_1$-$C_{10}$ alkylsulfonyl, —(CH$_2$)$_m$—O—(C$_1$-C$_{10}$ alkyl) wherein m is from 1 to 8, aryl, substituted aryl, substituted alkoxy, fluoroalkyl, heterocyclic radical, substituted heterocyclic radical, nitroalkyl, —NO$_2$, —CN, —NRC(O)—(C$_1$-C$_{10}$ alkyl), —C(O)—(C$_1$-C$_{10}$ alkyl), $C_2$-$C_{10}$ thioalkyl, —C(O)O—(C$_1$-C$_{10}$ alkyl), —OH, —SO$_2$, =S, —COOH, —NR$_2$, carbonyl, —C(O)—(C$_1$-C$_{10}$ alkyl)-CF$_3$, —C(O)—CF$_3$, —C(O)NR$_2$, —(C$_1$-C$_{10}$ alkyl)-S—(C$_6$-C$_{12}$ aryl), —C(O)—(C$_6$-C$_{12}$ aryl), —(CH$_2$)$_m$—O—(CH$_2$)$_m$—O—(C$_1$-C$_{10}$ alkyl) wherein each m is from 1 to 8, —C(O)NR$_2$, —C(S)NR$_2$, —SO$_2$NR$_2$, —NRC(O)NR$_2$, —NRC(S)NR$_2$, salts thereof, and the like. Each R as used herein is H, alkyl or substituted alkyl, aryl or substituted aryl, aralkyl, or alkaryl.

Curcumin, a polyphenolic compound derived from dietary spice turmeric, has a wide range of pharmacologic effects, including antioxidant, anti-inflammatory, anti-proliferative, and anti-angiogenic activities. However, due to its poor bioavailability, the clinical application of curcumin is limited. The structure of curcumin is:

Curcumin

To develop compounds with increased antioxidant activities, a series of novel compounds that have structural similarities to curcumin and possess novel structures have recently designed, synthesized, and screened. The following formula represents these novel compounds:

CLT010 wherein R₁ and R₂ are independently selected from the following table and may occupy one or more of the 2, 3, 5, or 6 positions on each respective aryl ring:

| R₁ | R₂ |
|---|---|
| H, lower alkyl, OH, OR₄, OAc | H, lower alkyl, OH, OR₄, OAc | wherein R₃ is one of:

wherein R₄ is H or a lower alkyl; and
wherein R₅ is H or a lower alkyl.

Among a series of compounds screened, in vitro assays have shown that CLT010-01, CLT010-07, and CLT010-12 have more potent anti-proliferative activities specific to capillary endothelial and cancer cells than curcumin and aminoguanidine (an inhibitor of inducible nitric oxide synthase).

These compounds do not significantly inhibit the growth of pericytes, suggesting specific inhibition to capillary endothelial cells. CLT010-01, CLT010-07, and CLT010-12 significantly inhibit TNF-α-stimulated generation of reactive oxygen species (ROS) and down-regulate the expression of VEGF in capillary endothelial cells, a pro-inflammation, angiogenic, and vascular permeability factor. Thus, these results show that the CLT010 curcumin analogs are useful as anti-angiogenic agents, anti-inflammatory, or anti-proliferative agents.

Moreover, these findings suggest that the CLT010 curcumin analogs, including CLT010-01, CLT010-07, and CLT010-12, have therapeutic potential in the treatment of oxidative stress and diseases that are caused or worsened by oxidative stress. Oxidative stress is implicated in many diseases. CLT010-01, CLT010-07, and CLT010-12 are useful to prevent or treat a number of diseases. For example, CLT010 curcumin analogs are shown to be useful in the treatment of ophthalmological diseases including age-related macular degeneration, diabetic retinopathy, diabetic macular edema, cystoid macular edema, retinopathy of prematurity, retinal vein occlusion, uveitis, retinitis pigmentosa, or USHER syndrome.

Moreover, because of the anti-proliferative effects of the CLT010 curcumin analogs, particularly CLT010-01, CLT010-07 and CLT010-12, these compounds are useful in the treatment and medicaments for cancers including prostate cancer, lung cancer, breast cancer, colorectal cancer, liver cancer, pancreatic cancer, lymphoma, multiple myeloma, or retinoblastoma.

Other disease states in which CLT010 compounds are useful in treatment include: metabolic disorders including diabetes mellitus, diabetic eye problems, diabetic foot, diabetic kidney problems, diabetic nerve problems, or diabetic teeth and gum problems; infectious and inflammatory diseases including bacterial infection, viral infection, arthritis (e.g., psoriatic arthritis, anklylosing spondvlitis, and rheumatoid arthritis), and rheumatism; skin inflammations and disorders; multiple sclerosis; immune system diseases including AIDS, allergies, asthma, lupus, scleroderma, or Sjogren's syndrome; heart and circulation system disease including arteriosclerosis, ischemia/reperfusion injury, tuberculosis, hypertension, congestive heart failure, venous insufficiency (pooling of blood in the veins; usually in the legs), peripheral vascular disease, or thrombosis; respiratory system diseases including chronic obstructive pulmonary disease, pulmonary edema, breathing difficulties, bronchopulmonary disease as cystic fibrosis, or chronic bronchitis; digestive system diseases including liver cirrhosis, chronic hepatitis, gastritis, or peptic ulcer; and brain and nervous system diseases including Alzheimer's disease, Parkinson's disease, neuroinflammation, or neurodegenerative disease.

According to embodiments, CLT010 compounds are included in a pharmaceutical composition together with additional active agents, carriers, vehicles, excipients, or auxiliary agents identifiable by a person skilled in the art upon reading of the present disclosure. According to embodiments, the CLT010 compounds comprises the following molecules together with at least a pharmaceutically acceptable carrier:

wherein R₁ and R₂ are independently selected from the following table and may occupy one or more of the 2, 3, 5, or 6 positions on each respective aryl ring:

| R₁ | R₂ |
|---|---|
| H, lower alkyl, OH, OR₄, OAc | H, lower alkyl, OH, OR₄, OAc | wherein $R_3$ is one of:

wherein $R_4$ is H or a lower alkyl; and
wherein $R_5$ is H or a lower alkyl.

According to embodiments, the CLT010 compounds comprise at least one of the following molecules together with at least a pharmaceutically acceptable carrier:

The pharmaceutical compositions comprise at least one pharmaceutically acceptable carrier. In such pharmaceutical compositions, the curcumin or CLT010 compounds form the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, intravitreal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates, or phosphates and agents for the adjustment of tonicity such as sodium chloride or dextrose. The pharmaceutical compositions can also be administered through ocular routes including: intravitreal, subconjunctival, intracameral, episcreal, retrobulbar, sub-tenon, or subretinal injections, or via topical eye drop. pH can be adjusted with acids or bases, such as hydrochloric acid or sodium hydroxide. The parenteral preparation can be enclosed in ampoules, disposable syringes, or multiple dose vials made of glass or plastic.

"Subject" as used herein refers to humans and non-human primates (e.g. guerilla, macaque, marmoset), livestock animals (e.g. sheep, cow, horse, donkey, pig), companion animals (e.g. dog, cat), laboratory test animals (e.g. mouse, rabbit, rat, guinea pig, hamster), captive wild animals (e.g. fox, deer), and any other organisms who can benefit from the agents of the present disclosure. There is no limitation on the type of animal that could benefit from the presently described agents. A subject regardless of whether it is a human or non-human organism may be referred to as a patient, individual, animal, host, or recipient.

Pharmaceutical compositions suitable for an injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. According to embodiments, isotonic agents, for example, sugars, polyalcohols such as manitol, sorbitol, or sodium chloride in the composition are added. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preparation is prepared by vacuum drying or freeze-drying, which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or strawberry, cherry, grape, lemon, or orange flavoring.

For administration by inhalation, the compounds are delivered in the form of an aerosol spray from pressured container or dispenser which contains a suitable propellant, e.g., a gas such as carbon dioxide, or a nebulizer.

According to embodiments, intravitreal injection is accomplished using PLGA-based microparticles or nanoparticles (liposomes). PEG-based formulas may also be used. Accordingly, the other methods for injectable pharmaceutical compositions are expressly contemplated for intravitreal injection.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In addition to the other forms of delivery, the compounds are deliverable via eye drop or intraocular injection. With respect to eye drops, the compositions of the present disclosure optionally comprise one or more excipients intended for topical application to the eye or nose. Excipients commonly used in pharmaceutical compositions intended for topical application to the eyes, such as solutions or sprays, include, but are not limited to, tonicity agents, preservatives, chelating agents, buffering agents, surfactants and antioxidants. Suitable tonicity-adjusting agents include mannitol, sodium chloride, glycerin, sorbitol and the like. Suitable preservatives include p-hydroxybenzoic acid ester, benzalkonium chloride, benzododecinium bromide, polyquaternium-1 and the like. Suitable chelating agents include sodium edetate and the like. Suitable buffering agents include phosphates, borates, citrates, acetates and the like. Suitable surfactants include ionic and nonionic surfactants, though nonionic surfactants are preferred, such as polysorbates, polyethoxylated castor oil derivatives and oxyethylated tertiary octylphenol formaldehyde polymer (tyloxapol). Suitable antioxidants include sulfites, ascorbates, BHA and BHT. The compositions of the present disclosure optionally comprise an additional active agent. With the exception of the optional preservative ingredient (e.g., polyquaternium-1), the compositions of the present disclosure preferably do not contain any polymeric ingredient other than polyvinylpyrrolidone or polystyrene sulfonic acid.

When the compositions of the present disclosure contain polyvinylpyrrolidone, the polyvinylpyrrolidone ingredient is preferably selected or processed to minimize peroxide content. Freshly produced batches of polyvinylpyrrolidone are preferred over aged batches. Additionally, particularly in cases where the composition will contain greater than 0.5% polyvinylpyrrolidone, the polyvinylpyrrolidone ingredient should be thermally treated (i.e., heated to a temperature above room temperature) prior to mixing with olopatadine in order to reduce the amount of peroxides in the polyvinylpyrrolidone ingredient and minimize the effect of peroxides on the chemical stability of olopatadine. While thermally treating an aqueous solution of polyvinylpyrrolidone for prolonged periods will substantially reduce the amount of peroxides, it can lead to discoloration (yellow to yellowish-brown) of the polyvinylpyrrolidone solution. In order to substantially reduce or eliminate peroxides without discoloring the polyvinylpyrrolidone solution, the pH of the aqueous solution of polyvinylpyrrolidone should be adjusted to pH 11-13 before it is subjected to heat. Much shorter heating times are needed to achieve significant reductions in peroxide levels if the pH of the polyvinylpyrrolidone solution is elevated.

One suitable method of thermally treating the polyvinylpyrrolidone ingredient is as follows. First, dissolve the polyvinylpyrrolidone ingredient in purified water to make a 4-6% solution, then raise the pH of the solution to pH 11-13, (an effective range of pH is 11-11.5), then heat to a temperature in the range of 60-121° C., preferably 65-80° C. and most preferably 70-75° C. The elevated temperature should be maintained for approximately 30-120 minutes (preferably 30 minutes). After the heated solution cools to room temperature, add HCl to adjust the pH to 3.5-8, depending upon the target pH for the olopatadine composition.

Particularly for compositions intended to be administered as eye drops, the compositions preferably contain a tonicity-adjusting agent in an amount sufficient to cause the final composition to have an ophthalmically acceptable osmolality (generally 150-450 mOsm, preferably 250-350 mOsm). The ophthalmic compositions of the present disclosure preferably have a pH of 4-8, preferably a pH of 6.5-7.5, and most preferably a pH of 6.8-7.2.

The eye-drop compositions of the present disclosure are preferably packaged in opaque plastic containers. A preferred container for an ophthalmic product is a low-density polyethylene container that has been sterilized using ethylene oxide instead of gamma-irradiation.

With respect to ophthalmic injectables, the pharmaceutical compositions of this disclosure are administered to the area in need of treatment by subconjunctival administration. One preferred method of subconjunctival administration to the eye is by injectable formulations comprising the pharmaceutical compositions disclosed herein. Another preferred method of subconjunctival administration is by implantations comprising slow releasing compositions.

Compositions that are delivered subconjunctivally comprise, according to embodiments, an ophthalmic depot formulation comprising an active agent for subconjunctival administration. According to embodiments, the ophthalmic depot formulation comprises microparticles of essentially pure active agent, e.g., the curcumin analogs disclosed herein, such as the CLT010 compounds. The microparticles comprising can be embedded in a biocompatible pharmaceutically acceptable polymer or a lipid encapsulating agent. The depot formulations may be adapted to release all of substantially all the active material over an extended period of time. The polymer or lipid matrix, if present, may be adapted to degrade sufficiently to be transported from the site of administration after release of all or substantially all the active agent. The depot formulation can be liquid formulation, comprising a pharmaceutical acceptable polymer and a dissolved or dispersed active agent. Upon injection, the polymer forms a depot at the injections site, e.g., by gelifying or precipitating.

Solid articles suitable for implantation in the eye can also be designed in such a fashion to comprise polymers and can be bioerodible or non-bioerodible. Bioerodible polymers that can be used in preparation of ocular implants carrying the compositions of the present disclosure include without restriction aliphatic polyesters such as polymers and copolymers of poly(glycolide), poly(lactide), poly(.epsilon.-caprolactone), poly(hydroxybutyrate) and poly(hydroxyvalerate), polyamino acids, polyorthoesters, polyanhydrides, aliphatic polycarbonates and polyether lactones. Illustrative of suitable non-bioerodible polymers are silicone elastomers.

According to embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein and according to embodiments, a therapeutically effective amount of the active compound (i.e., an effective dosage) may range from about 0.001 µg/kg to about 1 g/kg body weight. The skilled artisan will appreciate that certain factors can influence the dosage and timing required to effectively treat a subject, including but not limited to the severity of the disease or disorder, previous treatments, the general health or age of the subject, and other diseases present. As such, the actual dosage may be adjusted by artisans as well known and understood by artisans.

According to another aspect, one or more kits of parts can be envisioned by the person skilled in the art, the kits of parts to perform at least one of the methods herein disclosed, the kit of parts comprising two or more compositions, the compositions comprising alone or in combination an effective amount of curcumin or CLT010 compounds disclosed herein according to the at least one of the methods disclosed herein.

The kits possibly include also compositions comprising active agents other than the CLT010 or related molecules disclosed herein, identifiers of a biological event, or other compounds identifiable by a person skilled upon reading of the present disclosure. The term "identifier" refers to a molecule, metabolite, or other compound, such as antibodies, DNA or RNA oligonucleotides, able to discover or determine the existence, presence, or fact of or otherwise detect a biological event under procedures identifiable by a person skilled in the art; exemplary identifiers are antibodies, exemplary procedures are western blot, nitrite assay and RT-PCR, as described in the Examples.

According to embodiments, methods are disclosed for the treatment of inflammation, angiogenesis, or neovascularization for eye-related diseases using the agents disclosed herein. According to the methods, the compounds are provided in a therapeutically effective amount to treat the eye-related disease.

According to similar disclosures, the curcumin analogs may be provided or used to treat any disease state dependent, at least in part, on an oxidative stress pathway. Such disease states include those listed above.

According to other methods, the compounds of the present disclosure may be provided for or included in the manufacture of medicaments useful in treating diseases, including opthalmological diseases. According to still other methods, the compounds of the present disclosure may be provided for or included in the manufacture of medicaments useful in treating inflammatory diseases of all sorts, including those diseases listed above, as well as other diseases that are subject to an oxidative stress pathway.

EXAMPLES

Example 1

Chemical Structures of Novel Antioxidants

Figure 1:
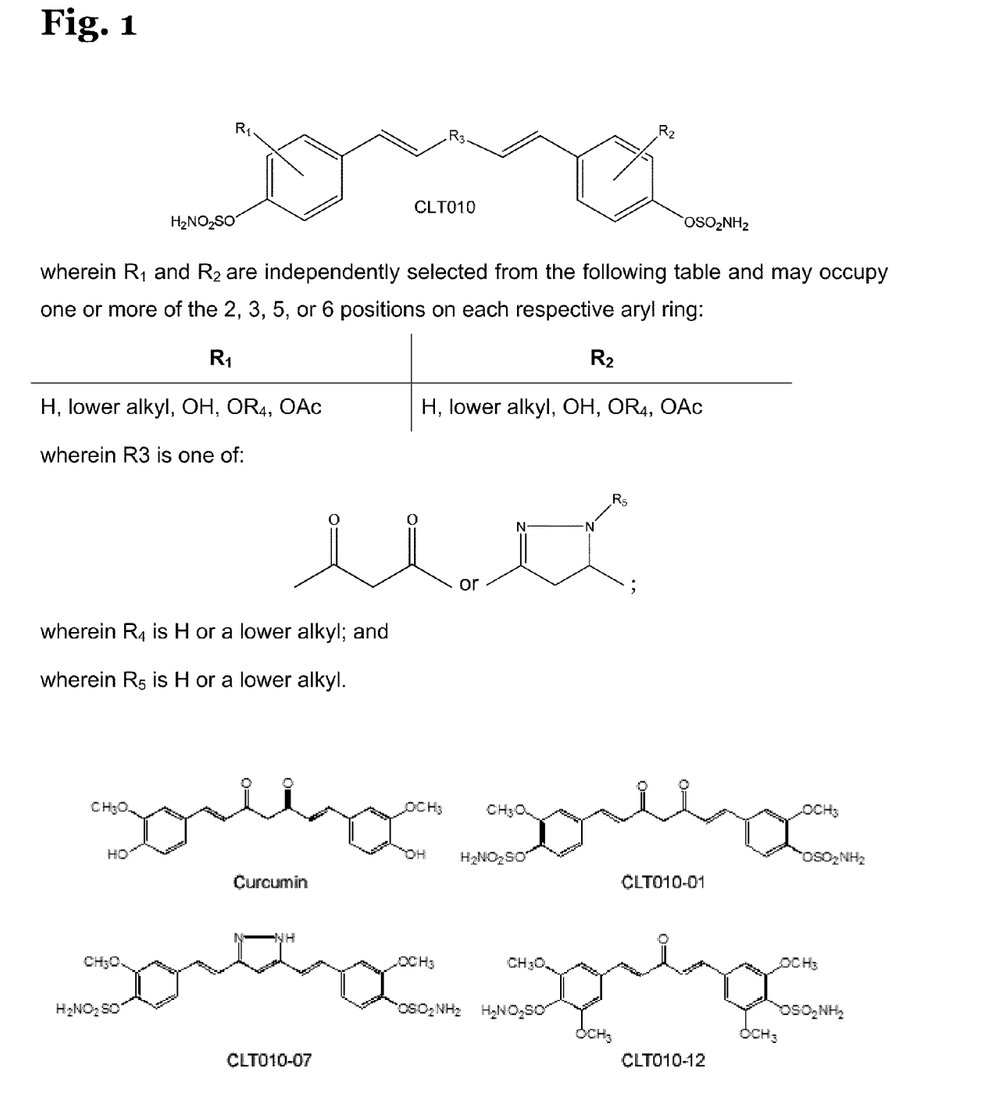
FIG. 1 are illustrations of embodiments of chemical structures of curcumin and curcumin analogs.

According to embodiments, a series of novel curcumin analogs have been recently designed, synthesized and screened and the activities of these compounds determined. The chemical structures of the curcumin analog antioxidants (CLT010 compounds) are shown in FIG. 1, including specific curcumin analogs CLT010-01, CLT010-07, CLT010-12.

Example 2

Novel Antioxidants are Substantially More Potent than Curcumin in Inhibiting the Proliferation of Retinal Capillary Endothelial and Cancer Cells Primary bovine retinal capillary endothelial cells (BRCECs), pericytes and human prostate adenocarcinoma cells (PC-3), and human breast cancer cells (MCF-7 and MDA-MB-231) were treated with the CLT010 compounds at various concentrations for 72 hours. Viable cells were quantified using MTT assay and $IC_{50}$ of each compound was calculated (mean±SD, n=3, Table 1). CLT010-01, CLT010-

07, and CLT010-12 inhibited the proliferation of BRCECs in a dose-dependent manner with the $IC_{50}$ of 3.6~9.7 µM, respectively. These compounds did not significantly inhibit the growth of pericytes, suggesting an endothelial cell specific inhibition. CLT010-07 and CLT010-12 also significantly inhibited the growth of cancer cells in a dose-dependent manner with the $IC_{50}$ of 0.6~6.7 µM. Curcumin had weaker effects on both BRCECs ($IC_{50}$=13.8 µM) and cancer cells ($IC_{50}$=9.5~25.6 µM). Aminoguanidine did not significantly inhibit the proliferation of BRCECs ($IC_{50}$>32 µM). These results indicated that novel compounds had more potent anti-proliferative effects than curcumin and aminoguanidine.

TABLE 1

Effect of aminoguanidine, curcumin and novel antioxidants on cell proliferation

| $IC_{50}$ (µM) | BRCEC | PC-3 | PC-3M | Du145 | MCF-7 | MDA-MB-231 |
|---|---|---|---|---|---|---|
| Aminoguanidine | >32 | | | | | |
| Curcumin | 13.8 ± 1.1 | 9.5 ± 1.6 | 10.7 ± 1.3 | 20.7 ± 3.5 | 21.5 ± 4.7 | 25.6 ± 4.8 |
| CLT010-01 | 9.7 ± 0.6 | 15.8 ± 1.6 | 8.5 ± 0.5 | 25.9 ± 0.3 | 5.5 ± 1.2 | 3.1 ± 1.3 |
| CLT010-07 | 3.9 ± 0.1 | 1.8 ± 0.3 | 6.7 ± 0.7 | 5.3 ± 2.4 | 6.5 ± 0.1 | 6.2 ± 1.6 |
| CLT010-12 | 3.6 ± 0.2 | 1.9 ± 0.04 | 4.2 ± 0.1 | 6.3 ± 0.2 | 1.5 ± 0.1 | 0.6 ± 0.1 |

Example 3

CLT010-01, CLT010-07 and CLT010-12 Significantly Inhibit TNF-α-Stimulated the Generation of Reactive Oxygen Species The intracellular generation of ROS was stimulated by TNF-α. Human retinal pigment epithelial cells (ARPE-19) were cultured on 96-well plates and pretreated with or without aminoguanidine, curcumin, and the CLT010 compounds for 24 h. TNF-α was added into culture medium at the concentration of 20 ng/ml and incubated with the cells for 1 h at 37° C. To measure ROS generation, 5-(and -6)-chloromethyl-2',7'-dichlorodihydrofluorescein diacetate (CM-$H_2$DCFDA) was added to the cells and incubated for 45 min. The relative fluorescence intensity representing the intracellular generation of ROS was measured using FLUOstar Omega at an emission wavelength of 535 nm, after excitation at 485 nm. TNF-α stimulated the intracellular generation of ROS by 36.9±8.4%, compounded with the untreated cells. Novel antioxidants reduced the intracellular ROS. At concentration of 8 µM, CLT010-01 reduced ROS by 40.5±6.3% ($p<0.01$, n=6), and CLT010-07 reduced ROS by 50.6±6.8% ($p<0.01$, n=6). CLT010-12 reduced ROS by 15.3±2.9 (($p<0.05$, n=6), 32.9±5.9 ($p<0.01$, n=6) and 55.1±3.9% ($p<0.01$, n=6) at 2, 4 and 8 µM, respectively (FIG. 2B). Under the same conditions, aminoguanidine and curcumin did not significantly affect the ROS production in the same concentration range (FIGS. 2A and 2B). These results suggest that CLT010-01, CLT010-07 and CLT010-12 have more potent antioxidant effects than aminoguanidine and curcumin.

Figure 2:
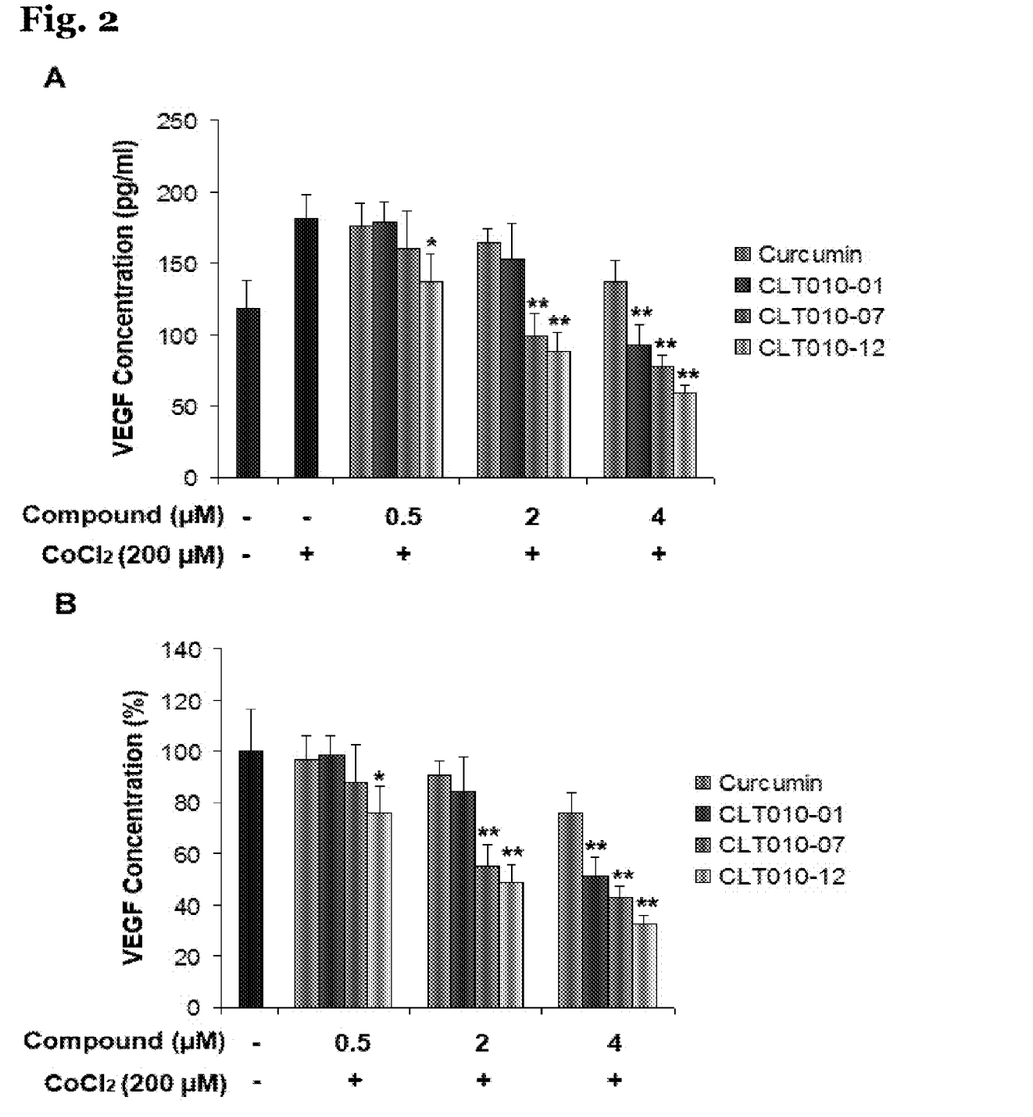
FIG. 2 are graphs of embodiments of experimental data showing the effect of novel antioxidants on the generation of reactive oxygen species.

According to embodiments of experimental data shown in FIG. 2, ARPE-19 cells were pretreated with aminoguanidine, curcumin, CLT010-01, CLT010-07, and CLT010-12 at indicated concentrations for 24 h prior to the addition of TNF-α (20 ng/ml). The cells were incubated with CM-$H_2$DCFDA for 45 min. The relative fluorescent intensity was measured as shown in FIG. 2A. Relative fluorescent intensity in the untreated cells, TNF-α-stimulated cells and compound plus TNF-α-treated cells. In FIG. 2B, the percentage of relative fluorescent intensity in each compound plus TNF-α-treated cells compared with that of TNF-α-stimulated cells is shown as the compound plus TNF-α vs TNF-α alone: *$p<0.05$, $p<0.01$, n=6.

Example 4

CLT010-01, CLT010-07 and CLT010-12 Down-Regulate VEGF Expression

To address if new antioxidants block VEGF over-expression induced by hypoxia, we measured levels of VEGF in human retinal capillary endothelial cells (HRCECs) after the exposure of CLT010-01, CLT010-07, and CLT010-12. The effect of new oxidants was compared with curcumin. HRCECs were seeded at a density of $4\times10^4$ cells/well in 400 µl of growth medium in triplicate in gelatin-coated 24-well plates, 24 h prior to the experiments. VEGF over-expression was induced by 200 µM of cobalt chloride ($CoCl_2$). Cells were incubated with the medium in the presence or absence of $CoCl_2$ and $CoCl_2$ plus curcumin, CLT010-01, CLT010-07 and CLT010-12 at the concentrations of 0.5, 2, and 4 µM. The conditioned medium was collected 24 h after treatment. VEGF concentrations were measured by ELISA specific for VEGF using a commercial kit (R & D Systems, Minneapolis, Minn.). $CoCl_2$ induced VEGF over-expression by 53.1±13.9%, compared to the untreated cells. The novel antioxidants reduced the expression of VEGF (FIGS. 3A and 3B). CLT010-01 reduced the VEGF levels by 48.8±7.8% at 4 µM ($p<0.001$, n=3). CLT010-07 inhibited the VEGF levels by 45.2±8.5 ($p<0.01$, n=3) and 57.2±4.4% ($p<0.001$, n=3) at 2 and 4 µM, respectively. CLT010-12 suppressed the VEGF expression by 24.2±10 ($p<0.01$, n=3), 58.2±7.2 ($p<0.001$, n=3), and 67.3±4.4% ($p<0.001$, n=3) at 0.5, 2 and 4 µM ($p<0.001$, n=3), respectively (FIG. 3B). Curcumin did not significantly inhibit the release of VEGF from cells into medium under same concentrations ($p>0.05$, n=3) (FIGS. 3A and B). These results indicate that the new antioxidants CLT010-01, CLT010-07, and CLT010-12 have more potent anti-VEGF activity than curcumin.

Figure 3:
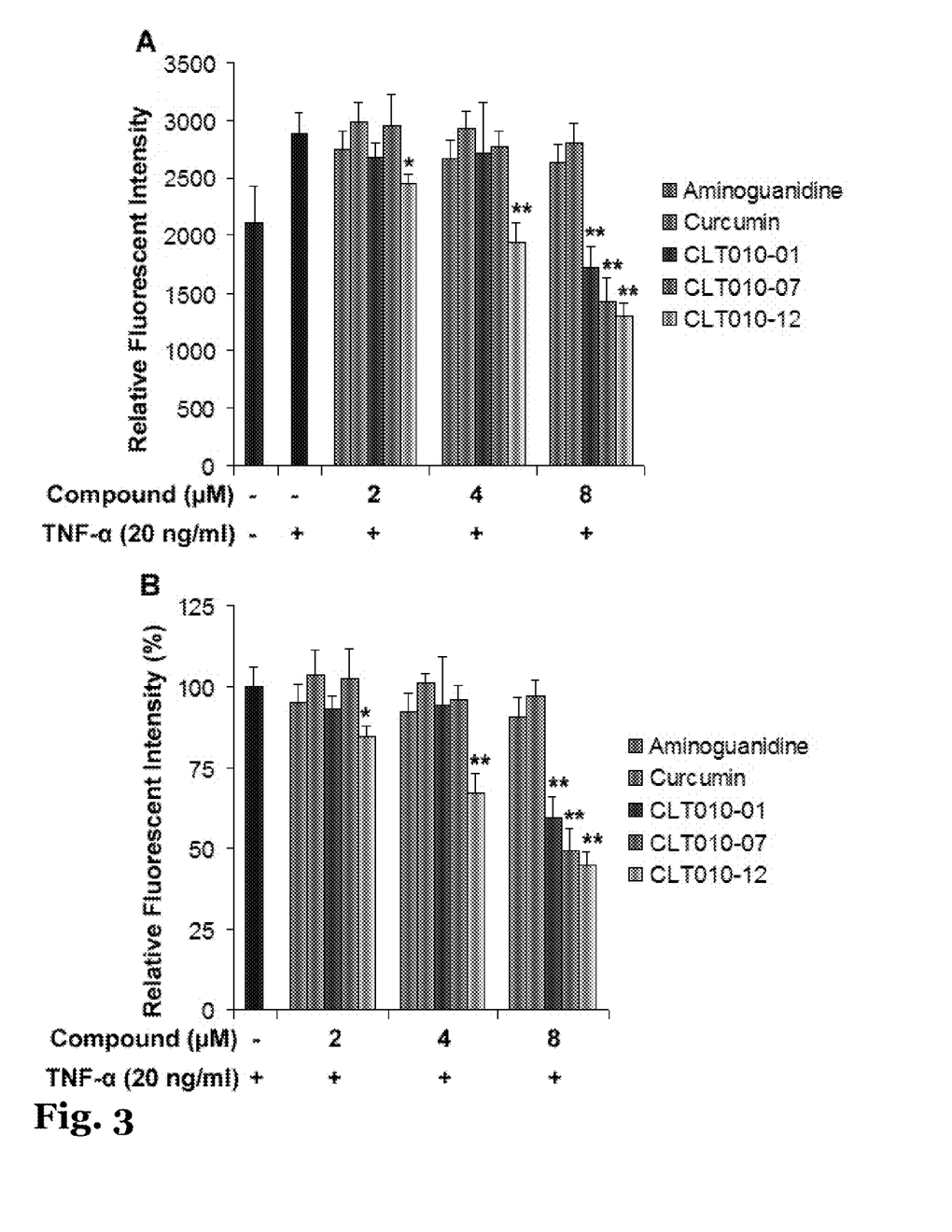
FIG. 3 are graphs of embodiments of experimental data showing CLT010-01, CLT010-07, and CLT010-12 down-regulating the expression of VEGF in HRCECs.

According to embodiments of experimental data shown in FIG. 3, HRCECs were cultured in the presence or absence of $CoCl_2$, $CoCl_2$ plus curcumin, CLT010-01, CLT010-07, and CLT010-12 at concentrations as indicated. The conditioned medium was collected after 24 h treatment. VEGF levels were measured by ELISA. In FIG. 3A, VEGF concentrations in the medium from the untreated cells, $CoCl_2$-treated cells, and $CoCl_2$ plus compound-treated cells are shown. In FIG. 3B, the percentage of VEGF concentrations in the medium from $CoCl_2$ plus compound-treated cells compared with that of the medium from $CoCl_2$-treated cells is shown. $CoCl_2$ plus compounds plus vs. $CoCl_2$: *$p<0.01$, $p<0.001$, n=3.

Example 5

Synthesis of Curcumin and Generic Curcumin Analogs

Curcumin and curcumin analogs may be synthesized according to the following scheme:

Example 6

Synthesis of Curcumin Analog with a Sulfonamide Group

Curcumin analogs having a sulfonamide group may be synthesized according to the following scheme starting from curcumin:

CLT010-01

Synthesis of CLT010-12 proceeds the same, but with the starting compound:

instead of curcumin.

Example 7

Synthesis of CLT010-07

CLT010-07 may be synthesized according to the following scheme:

The invention claimed is:

1. A composition comprising:
a compound having the formula:

and a pharmaceutically acceptable carrier.

2. A method comprising:
providing to an animal having an eye disease characterized by neovascularization an effective amount of the composition of claim 1 for the treatment of the eye disease.

3. The method of claim 2, wherein the disease the eye disease is diabetic retinopathy.

4. A method of treating prostate cancer comprising providing to an animal having prostate cancer an effective amount of the composition of claim 1 for the treatment of the prostate cancer.

5. A method of treating breast cancer comprising providing to an animal having breast cancer an effective amount of the composition of claim 1 for the treatment of the breast cancer.

* * * * *